(12) United States Patent
Wilson et al.

(10) Patent No.: US 6,569,198 B1
(45) Date of Patent: May 27, 2003

(54) MITRAL OR TRICUSPID VALVE ANNULOPLASTY PROSTHETIC DEVICE

(76) Inventors: Richard A. Wilson, 2351 Palisades Crest Dr., Lake Oswego, OR (US) 97034; Daniel J. Wilson, 2351 Palisades Crest Dr., Lake Oswego, OR (US) 97034

( * ) Notice: Subject to any disclaimer, the term of this patent is extended or adjusted under 35 U.S.C. 154(b) by 0 days.

(21) Appl. No.: 09/823,501

(22) Filed: Mar. 30, 2001

Related U.S. Application Data

(60) Provisional application No. 60/193,427, filed on Mar. 31, 2000.

(51) Int. Cl.$^7$ .................................................. A61F 2/24
(52) U.S. Cl. ..................... 623/2.37; 623/2.36; 623/2.38; 623/904
(58) Field of Search ............................. 623/2.36, 2.37, 623/2.38, 2.39, 2.4, 900, 904

(56) References Cited

U.S. PATENT DOCUMENTS

| | | | |
|---|---|---|---|
| 3,656,185 A | 4/1972 | Carpentier | 3/1 |
| 4,042,979 A | 8/1977 | Angell | 3/1.5 |
| 4,055,861 A | 11/1977 | Carpentier et al. | 3/1.5 |
| 4,164,046 A | 8/1979 | Cooley | 3/1.5 |
| 4,290,151 A | 9/1981 | Massana | 3/1.5 |
| 4,489,446 A | 12/1984 | Reed | 3/1.5 |
| 4,602,911 A | 7/1986 | Ahmadi et al. | 623/2 |
| 4,917,698 A | 4/1990 | Carpentier et al. | 623/2 |
| 5,201,880 A | 4/1993 | Wright et al. | 623/2 |
| 5,306,296 A | 4/1994 | Wright et al. | 623/2 |
| 5,350,420 A | 9/1994 | Cosgrove et al. | 623/2 |
| 5,593,424 A | 1/1997 | Northrup, III | 606/232 |
| 5,607,471 A * | 3/1997 | Seguin et al. | 623/2.36 |
| 5,617,854 A | 4/1997 | Munsif | 128/642 |
| 5,824,066 A | 10/1998 | Gross | 623/2 |
| 5,876,419 A | 3/1999 | Carpenter et al. | 606/198 |
| 5,961,539 A | 10/1999 | Northrup, III et al. | 606/232 |
| 5,980,552 A | 11/1999 | Pinchasik et al. | 606/198 |
| 6,027,525 A | 2/2000 | Suh et al. | 623/1 |
| 6,102,945 A | 8/2000 | Campbell | 623/2.37 |
| 6,143,024 A | 11/2000 | Campbell et al. | 623/2.36 |
| 6,174,332 B1 | 1/2001 | Loch et al. | 623/2.37 |
| 6,187,040 B1 | 2/2001 | Wright | 623/2.36 |
| 6,210,432 B1 | 4/2001 | Solem et al. | 623/1.15 |
| 6,217,610 B1 * | 4/2001 | Carpentier et al. | 623/2.37 |
| 6,250,308 B1 * | 6/2001 | Cox | 623/2.36 |

FOREIGN PATENT DOCUMENTS

WO  WO-97/40755 A1 * 11/1997

OTHER PUBLICATIONS

Braunwald, Eugene, et al., Eds., *Heart Disease: A Textbook of Cardiovascular Medicine* (6th Edition), Chapter 46, "Valvular Heart Disease," pp. 1643–1713. [Specifically pp. 1660–1665 (mitral regurgitation treatment) and pp. 1693–1694 (tricuspid regurgitation)].

\* cited by examiner

*Primary Examiner*—Paul B. Prebilic
(74) *Attorney, Agent, or Firm*—Stoel Rives LLP

(57) ABSTRACT

A prosthetic device inserted into a blood vessel decreases the severity of valve regurgitation during ventricular contraction. The prosthetic device reduces the circumference of the valve annulus, causing the valve leaflets attached to the annulus to close more completely. A first preferred embodiment is an elongated member that includes distal and proximal segments separated by an intermediate segment. The prosthetic device has at least one anchor control wire to anchor the device in the blood vessel and at least one length control wire. A second preferred embodiment is an elongated member that includes distal and proximal segments that are connected by a pivot or hinge joint. A control wire is anchored on the distal segment and pivotally moves the distal and proximal segments closer together. Rotation of the length control wire of the first embodiment or the control wire of the second embodiment reduces the circumference of the valve annulus.

9 Claims, 7 Drawing Sheets

MITRAL OR TRICUSPID VALVE ANNULOPLASTY PROSTHETIC DEVICE

RELATED APPLICATIONS

This application derives priority from U.S. Provisional Patent Application No. 60/193,427, filed Mar. 31, 2000.

TECHNICAL FIELD

This invention relates to the repair of mitral and tricuspid valves exhibiting valve regurgitation and more particularly to a device and method suitable for a less invasive repair of a mitral or tricuspid heart valve.

BACKGROUND OF THE INVENTION

Human beings have a closed circulatory system in which oxygen-rich blood is almost completely segregated from oxygen-poor blood. The primary purpose of the circulatory system, which is also referred to as the cardiovascular system and consists of the heart, blood vessels, and blood, is to provide oxygenated blood to the organs throughout the body and to the lungs. The heart contains two ventricles, which are chambers that pump blood out of the heart and into arteries that carry blood away from the heart and into the organs throughout the body. The heart also contains two atria, which are chambers that receive blood returning from the body. Veins carry the blood returning from the body into the right atrium. During a period called diastole, the blood from the right atrium drains into the right ventricle. The right ventricle then contracts during a period called systole and pumps blood through the pulmonic valve into the lungs. Oxygen-rich blood returns from the lungs via the pulmonary veins and fills the left atrium. During diastole, blood drains from the left atrium into the left ventricle. During systole, the left ventricle powerfully contracts and pumps the oxygen-rich blood into the aorta, which carries the oxygen-rich blood to arteries that carry the oxygen-rich blood to the organs throughout the body.

Between each atrium and ventricle is an atrioventricular valve that prevents the backflow of blood into the atrium during ventricular contraction. The atrioventricular valves on the left-hand and right-hand sides of the heart are known as, respectively, the mitral and tricuspid valves.

The mitral valve is located between the left atrium and the left ventricle and allows unidirectional blood flow from the atrium to the ventricle. The mitral valve has two leaflets that are attached to a semi-rigid ring or annulus. FIG. 1 is a pictorial diagram of the mitral valve annulus as viewed from within the left atrium. A coronary sinus 2 lies adjacent to a mitral valve annulus 4, to which is attached an anterior leaflet 6 and a posterior leaflet 8.

In a healthy heart, the anterior and posterior leaflets 6 and 8 close tightly during systole, the period of left ventricular contraction in which the left ventricle contracts to pump blood out of the heart into the body via the aorta. When functioning properly, the anterior and posterior leaflets 6 and 8 do not allow any of the blood being ejected from the left ventricle to flow backwards through the mitral valve into the left atrium. However, one consequence of a number of cardiac diseases is that mitral valve annulus 4 becomes dilated so that the anterior and posterior leaflets 6 and 8 cannot completely close during systole, thereby creating gaps 10 between the anterior and posterior leaflets 6 and 8. As a result, mitral valve regurgitation occurs, resulting in some of the blood being ejected from the left ventricle flowing backwards through the incompletely closed mitral valve leaflets and into the left atrium. The blood that flows backwards during mitral valve regurgitation increases the pressure in the left atrium and in the pulmonary veins and the lungs. The result of this increased pressure is congestion in the lungs, a major cause of congestive heart failure. Dilation of the mitral valve also results in distortion of the shape of the valve orifice. Decreasing the circumference of the dilated mitral valve annulus has been shown to decrease the severity of mitral valve regurgitation, which results in a decrease in morbidity caused by congestive heart failure.

Prior art attempts to decrease the severity of mitral valve regurgitation entail replacement or repair of the mitral valve. Valve replacement and repair have several drawbacks. Both procedures require open-heart surgery, which necessitates stopping the heart and diverting the bloodstream through a heart-lung machine (a process referred to as cardiopulmonary bypass). Open heart surgery is a very intrusive procedure with many potential complications and a long recovery time. Besides the risk of death or stroke, there is an increased risk of diminished cognitive function after cardiopulmonary bypass.

In the case of mitral valve replacement, the native mitral valve is surgically removed and is replaced by an artificial mitral valve sewn into the mitral valve annulus. Certain replacement valves have a high failure rate, and a consequent increased rate of morbidity. For example, the Bjork-Shiley 60-Degree and 70-Degree Convexo-Concave heart valves have received significant public attention because of their high failure rate. The flaw in the valves involves the metal struts that hold the curved disk that tilts back and forth inside the metal ring to regulate blood flow between the heart chambers. The struts have been shown to break, leading to valve failure.

In the case of mitral valve repair, a number of surgical techniques have been developed. The most common mitral valve repair entails sewing a mitral annuloplasty ring into the mitral valve annulus. The mitral annuloplasty ring has a smaller circumference than that of the portion of the dilated mitral valve annulus to which the ring is sutured. This suturing of the mitral valve annulus to the rigid or semi-rigid annuloplasty ring results in a "cinching up" or shortening of a portion of the circumference of the mitral valve annulus so that the mitral valve leaflets come together more completely during systole, thereby decreasing the severity of mitral valve regurgitation. There are various prostheses in use for mitral or tricuspid valve repair, and each of them has disadvantages.

Use of rigid annuloplasty ring prostheses is taught by Carpentier in U.S. Pat. No. 3,656,185 and Cooley in U.S. Pat. No. 4,164,046. Although widely used, these rigid angioplasty ring prostheses have received significant criticism regarding their inflexibility, which prevents the normal alteration in size and shape of the mitral annulus; their obstruction of the left ventricular outflow tract, which can decrease the dimensions of the left ventricular outflow tract; and the incidence of inflow obstruction, which is a complication usually associated with use of the rigid ring prosthesis in the tricuspid valve. In addition, rigid annuloplasty ring prostheses have the disadvantage of not being of adjustable size. Thus the surgeon has to accurately judge the correct size of ring needed to reduce the annulus circumference and produce a competent valve.

Adjustable annuloplasty rings have also been implemented, as taught by Reed in U.S. Pat. No. 4,489,446; Ahmadi, et al. in U.S. Pat. No. 4,602,911; and Angell in U.S. Pat. No. 4,042,979. Many of these adjustable rings have the disadvantage of being circular, which is not an appropriate shape, particularly for the mitral annulus.

Use of a flexible ring prosthesis is taught by Massana in U.S. Pat. No. 4,290,151; Carpentier, et al. in U.S. Pat. Nos. 4,055,861 and 4,917,698; Northup III in U.S. Pat. No. 5,593,424; Cosgrove, et al. in U.S. Pat. No. 5,350,420; Wright, et al. in U.S. Pat. No. 5,306,296; and Wright et al. in U.S. Pat. No. 5,201,880. One disadvantage of using the fully flexible annuloplasty ring is the fact that it can be shortened in the posterior segment only by the placement of plicating sutures. Judgment of the position, size, and spacing of these sutures requires skill and experience. Inappropriate suture placement in the anterior segment can cause undesirable intra-trigonal shortening. A second disadvantage of using the flexible ring prosthesis is that following the tightening of the drawstrings, a bulky knot is formed on the atrial surface of the ring. The knot lies directly in the blood flow path into the inflow side of the valve. Should a thrombus form on the knot, an embolus could result. Also, if the surplus drawstrings are cut too close to the knot, the knot may become undone. Conversely, should significant surplus drawstrings tails remain, abrasion of the valve leaflets could occur.

What is needed, therefore, is a safer and less traumatic method of decreasing the incidence of mitral or tricuspid valve regurgitation that does not necessitate open heart surgery, heart stoppage, cardiopulmonary bypass, or replacement valve insertion.

SUMMARY OF THE INVENTION

An object of the present invention is, therefore, to provide a less invasive, safer method of decreasing the severity of mitral or tricuspid valve regurgitation.

Different embodiments of the present invention, described by way of example, position a prosthetic device in a blood vessel, such as the coronary sinus surrounding the mitral valve annulus or the coronary vein surrounding the tricuspid valve annulus. The prosthetic device reduces the circumference of the mitral or tricuspid valve annulus causing the valve leaflets that attach to the annulus to close more completely, thereby decreasing the regurgitation of blood back through the incompletely closed valve leaflets during ventricular contraction. The prosthetic device may be inserted into a beating heart either percutaneously via the femoral, jugular, or subclavian vein or via the right atrium through a surgical incision in the vena cava without employing open heart surgery or cardiopulmonary bypass.

A first preferred embodiment of the prosthetic device is an elongated member that includes distal and proximal segments separated by an intermediate segment. Each of the distal and proximal segments has a recessed end into which a different end of the intermediate segment fits and a terminal end opposite the recessed end. A first rigid or semi-rigid length control wire or cable is anchored on the distal segment and has a threaded section that passes through a mated threaded aperture in the intermediate segment. Rotating the first length control wire causes the end of the intermediate segment to insert into or withdraw from the recessed end of the distal segment, thereby shortening or lengthening the prosthetic device. Optionally, a second length control wire that further aids in controlling the overall length of the prosthetic device may be attached to the intermediate segment nearer to the proximal segment. Attached to the distal and proximal segments are two anchor control wires, each of which is connected to a coil spring having a controllable pitch. The control anchor wires are concentrically wound around each of the terminal ends of the distal and proximal segments. Rotation of the anchor control wires widens or narrows the coil spring diameter to respectively anchor the prosthetic device to or disengage the prosthetic device from the coronary sinus.

A second preferred embodiment of the prosthetic device is an elongated member that includes distal and proximal segments that are connected by a pivot or hinge joint. The distal segment has a narrow intermediate section positioned between a free end section and an interior section in the form of a clevis fastener. The proximal segment has a narrowed end section and an interior tongue section that fits into the clevis fastener. A control wire anchored on the interior section of the distal segment has a threaded portion that passes through a mated threaded opening located on the tongue section of the proximal segment. Rotation of the control wire pivotally moves the distal and proximal segments closer to or farther from each other to, respectively, reduce or increase the circumference of the valve annulus. Reduction of the circumference of the valve annulus brings the two valve leaflets closer together and thereby decreases the severity of valve regurgitation.

Additional objects and advantages of this invention will be apparent from the following detailed description of preferred embodiments thereof which proceeds with reference to the accompanying drawings.

DETAILED DESCRIPTION OF THE PREFERRED EMBODIMENTS

Figure 2:
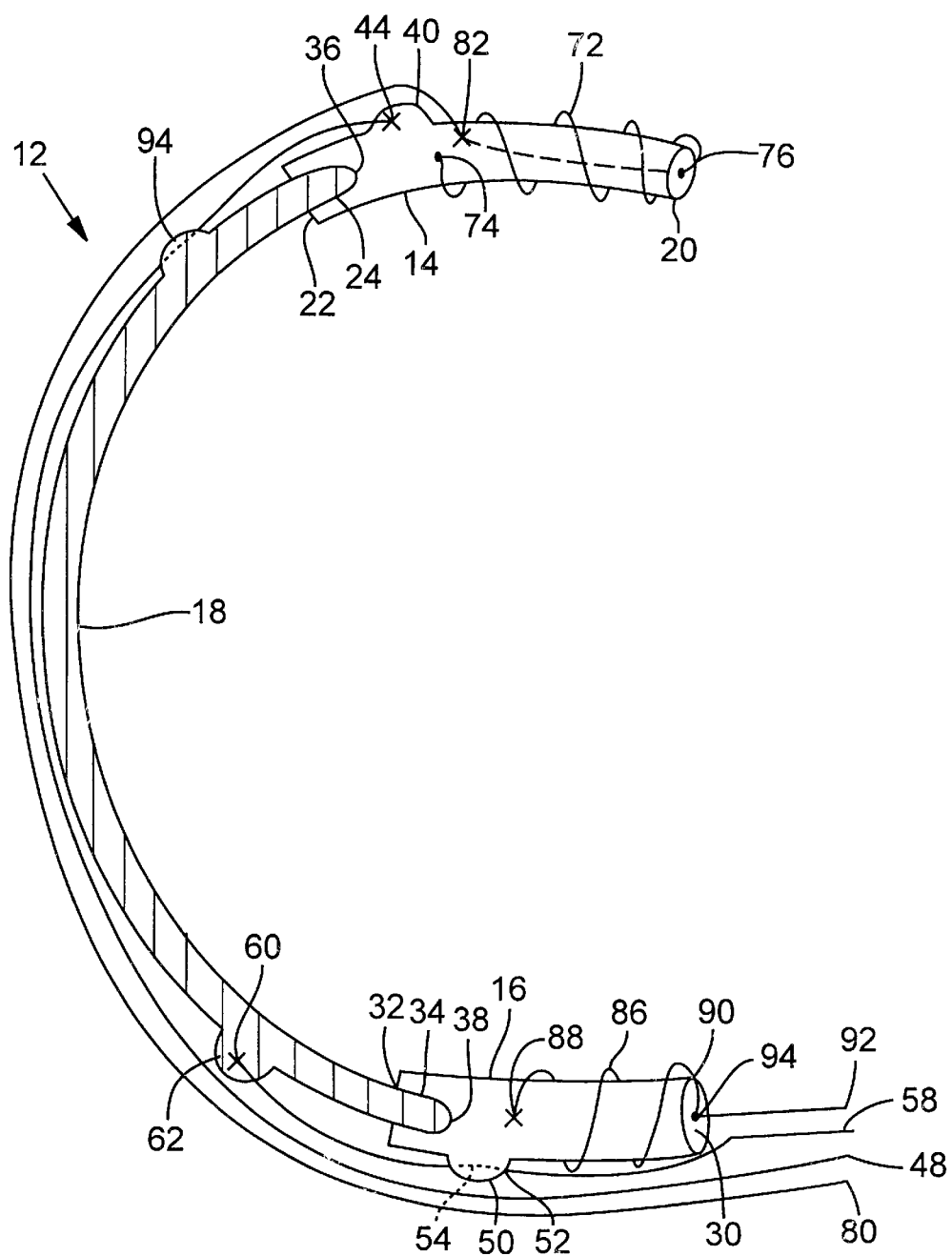
FIG. 2 is a side elevation view of a first embodiment of the prosthetic device of the present invention.

FIG. 2 is a schematic diagram of a first embodiment of the prosthetic device of the present invention. A prosthetic device 12 includes a distal segment 14 and a proximal segment 16 separated by an intermediate segment 18. The nomenclature identifying these components corresponds to their positions when prosthetic device 12 is placed in coronary sinus 2. The distal, proximal, and intermediate segments are aligned to define a longitudinal axis 19 (shown in FIGS. 3a, 3b, and 3c) of the prosthetic device which is made of a flexible material and, therefore, may be curved in response to an applied force. Each of distal segment 14 and proximal segment 16 is preferably about 27 mm in length, and intermediate segment 18 is preferably about 40 mm in length. Distal segment 14 has a terminal end 20 and a coupling end 22 into which a recessed region 24 is formed. Similarly, proximal segment 16 has a terminal end 30 and a coupling end 32 into which a recessed region 34 is formed. Each of distal segment 14 and proximal segment 16 is preferably about 2 mm wide. Intermediate segment 18 has a distal end 36 and a proximal end 38 that slidably fit for lengthwise movement within, respectively, recessed region 24 of coupling end 22 and recessed region 34 of coupling end 32.

Distal segment 14 includes a nub 40 that is positioned nearer to coupling end 22 and holds a spherical bearing 44 to which one end of a first length control wire 48 is attached. Proximal segment 16 includes a nub 50 that is positioned nearer to coupling end 32 and has a threaded aperture 52 through which a threaded section 54 of a second length control wire 58 passes before it is attached to a spherical bearing 60 in a nub 62 positioned near proximal end 38 of intermediate segment 18. Length control wires 48 and 58 control the extent to which distal end 36 and proximal end 38 are contained within the respective recessed regions 24 and 34 and thereby control the overall length of prosthetic device 12, in the manner described below with reference to FIGS. 3, 4, and 5.

Figure 3A:
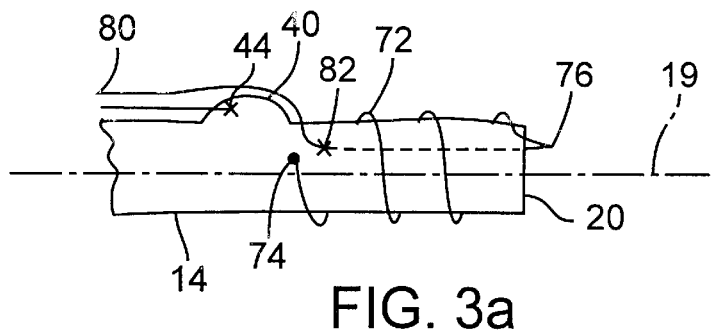
FIGS. 3a, 3b, and 3c are fragmentary enlarged views of, respectively, the distal segment, the proximal segment, and the intermediate segment of the prosthetic device shown in FIG. 2.
Figure 4A:
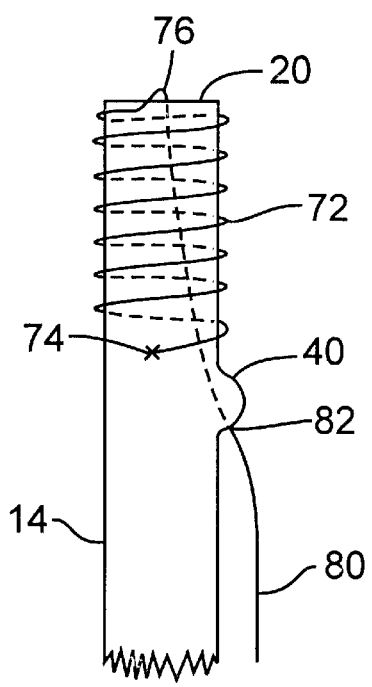
FIGS. 4a and 4b are schematic fragmentary views of the prosthetic device of FIG. 2 showing, respectively, the pre-insertion and post-insertion deployment of the distal coil spring.
Figure 4B:
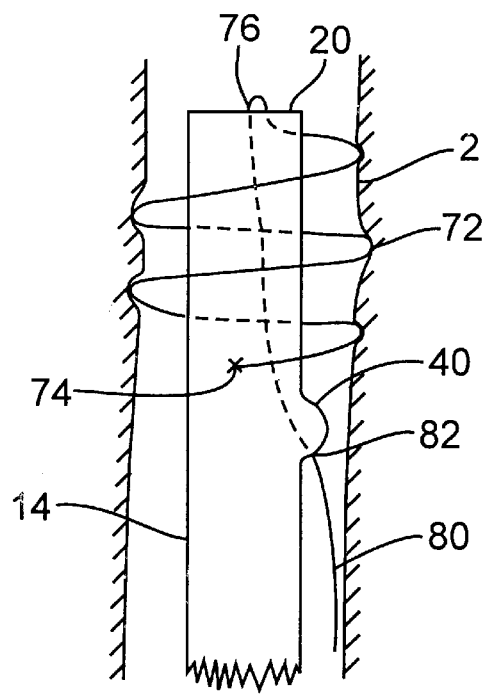

As is shown in FIG. 3a, distal segment 14 includes at its terminal end 20 an anchoring device that is preferably in the form of a coil spring 72. Coil spring 72 is anchored at one end 74 to the outer surface of distal segment 14 and connected at an opposite end 76 to one end of a first anchor control wire 80 that enters distal segment 14 through a threaded hole 82 and runs through the interior of distal segment 14. Coil spring 72 has a fixed axial length such that rotation of first anchor control wire 80 causes the radius of coil spring 72 to increase and its pitch to decrease. An increase in the radius of coil spring 72 causes it to impinge upon the coronary sinus 2, as is shown in comparative FIGS. 4a and 4b.

Figure 3B:
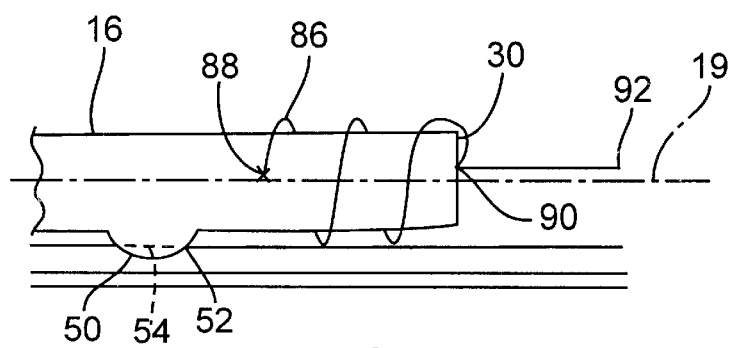

As is shown in FIG. 3b, proximal segment 16 includes at its terminal end 30 an anchoring device that is preferably in the form of a coil spring 86. Coil spring 86 is anchored at one end 88 to the outer surface of proximal segment 16 and connected at an opposite threaded end 90 to one mated threaded end of a second anchor control wire 92. Coil spring 86 has a fixed axial length such that rotation of second anchor control wire 92 causes the radius of coil spring 86 to increase and the pitch to decrease. An increase in the radius of coil spring 86 causes it to impinge upon coronary sinus 2, as discussed above.

Figure 3C:
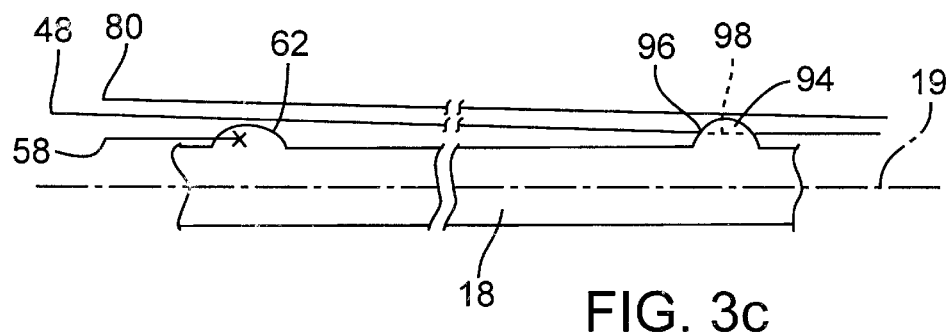

FIG. 3c is a fragmentary schematic view of intermediate segment 18 of prosthetic device 12. A nub 94 is positioned near distal end 36 of intermediate segment 18 and has a threaded aperture 96 through which a threaded section 98 of first length control wire 48 passes before it is attached to spherical bearing 44 in distal segment 14. Proximal segment 16 includes a nub 50 that is positioned nearer to coupling end 32 and has a threaded aperture 52 through which a threaded section 54 of a second length control wire 58 passes before it is attached to a spherical bearing 60 in a nub 62 positioned near proximal end 38 of intermediate segment 18. Rotation of either one of both of first and second length control wires, 48 and 58, respectively, results in extension or retraction of the two ends of intermediate segment 18 into distal recessed end 24 and proximal recessed end 34. Thus the overall length of prosthetic device 12 may be altered.

Figure 5:
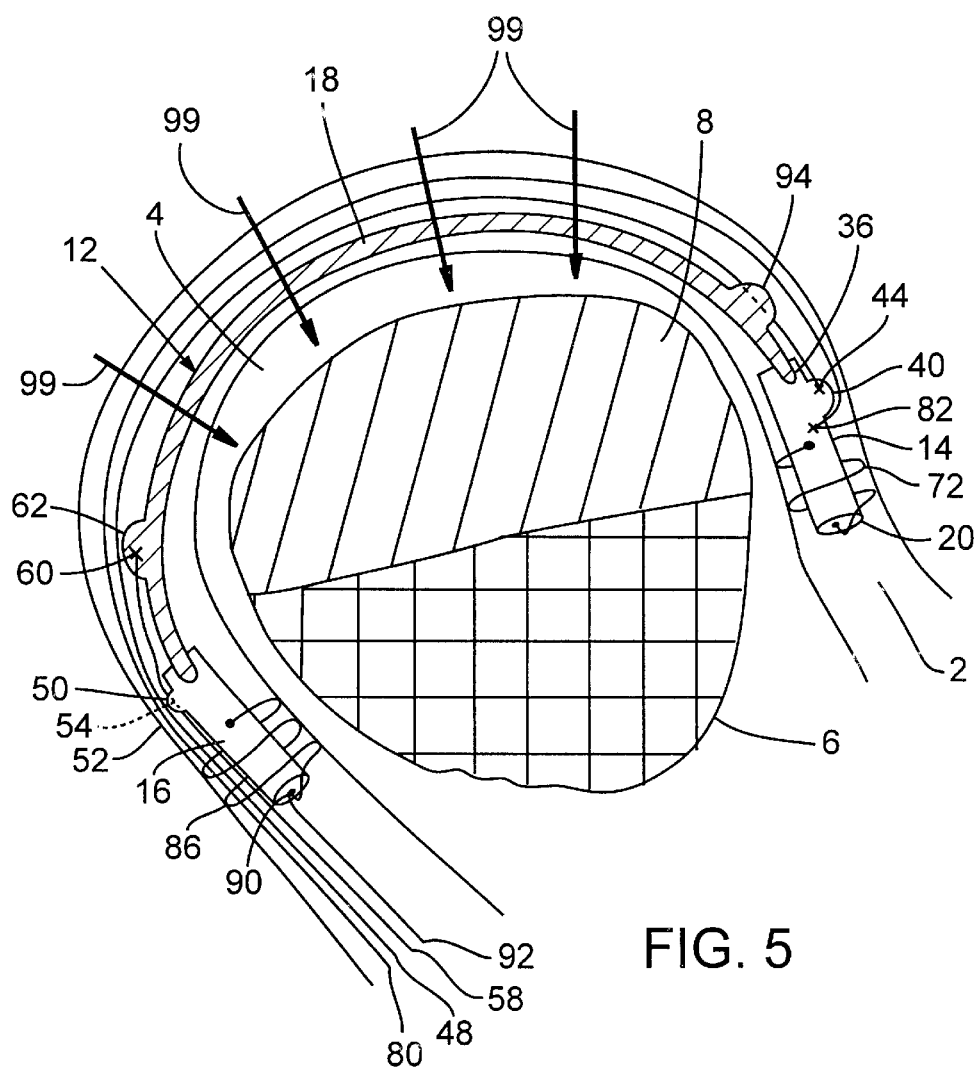
FIG. 5 is a schematic diagram of the prosthetic device of FIG. 2 deployed inside the coronary sinus.

FIG. 5 shows deployment of prosthetic device 12 in coronary sinus 2. Deployment of prosthetic device 12 entails insertion, distal segment 14 first, into coronary sinus 2. Such insertion may be done in one of two ways: (1) the prosthetic device may be inserted into the femoral vein, through the inferior vena cava and the lower portion of the right atrium, and then into the coronary sinus; or (2) the prosthetic device may be inserted into the subclavian vein located under the collarbone, through the superior vena cava and the right atrium, and then into the coronary sinus. Both procedures are preferably performed under fluoroscopic or echocardiographic guidance and through a guide catheter. The prosthetic device is then advanced into the coronary sinus and positioned such that the distal and proximal anchoring devices are located on opposite sides of the circumference of the valve annulus to be shortened.

Once prosthetic device 12 has been correctly positioned in coronary sinus 2, anchoring of the distal segment 14 of prosthetic device 12 in the anterior part of the coronary sinus or in the anterior cardiac vein is initiated. To this end, first anchor control wire 80 is twisted counter-clockwise, forcing coil spring 72 to expand and press against the walls of coronary sinus 2 to "anchor" prosthetic device 12. Once distal segment 14 is thought to be sufficiently anchored, the stability of coil spring 72 is tested by applying minor tension to first anchor control wire 80. While tension is being applied, anchoring of proximal segment 16 is effected. To this end, coil spring 86 is rotated counter-clockwise forcing it to expand and press against the walls of coronary sinus 2, thereby further anchoring prosthetic device 12.

Figure 1:
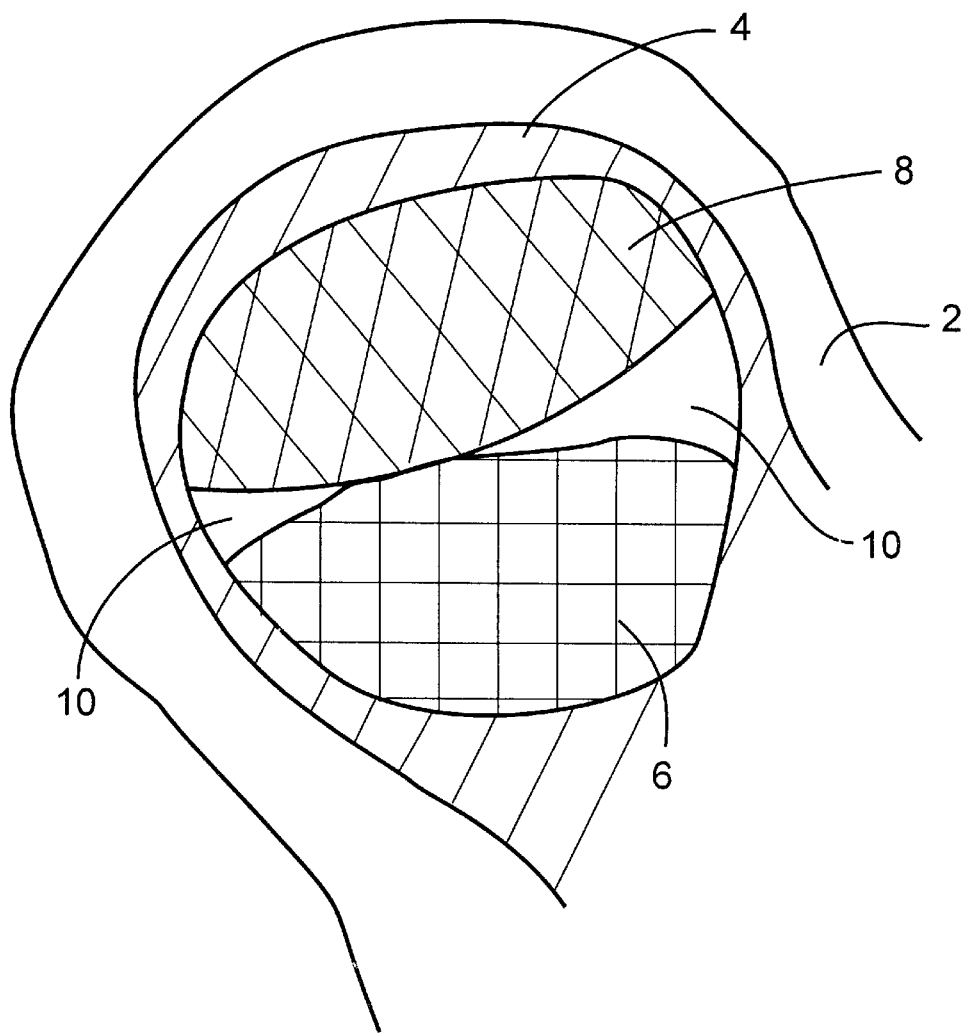
FIG. 1 shows in pictorial form the interrelationship of the coronary sinus, the mitral valve annulus, and the anterior and posterior leaflets of the mitral valve annulus as viewed from within the left atrium.

After both coil springs have been expanded and prosthetic device 12 is securely anchored within coronary sinus 2, the overall length of prosthetic device 12 can be adjusted as necessary. Such adjustment is effected by rotating either one or both of first and second length control wires 48 and 58 so that the overall length of prosthetic device 12 is decreased. The preferred decrease in length is about 1 to about 2 cm and can be monitored using transthoracic or transesophageal echocardiography at the time of the adjustment to guard against causing over-constriction of the valve annulus, which could result in stenosis of the valve leaflets. Decreasing the overall length of prosthetic device 12 decreases the circumference of valve annulus 4 and thereby results in radial application of an external force to valve annulus 4, indicated by the force arrows 99 in FIG. 5. This external radial force brings posterior leaflet 8 into closer and more complete contact with anterior leaflet 6, thus decreasing the severity of valve regurgitation through gap(s) 10 (shown in FIG. 1) during systole. The excess of length control and anchor control wires is tucked under the skin or the collarbone.

The second embodiment of the present invention is an elongated member that includes two hinged segments that can be used to manipulate the mitral or tricuspid valve annulus of the human heart. The hinged segments are aligned to define a longitudinal axis 19 (shown in FIG. 7) of the prosthetic device, which axis 19 may be curved in response to an applied force. The prosthetic device may be percutaneously inserted as discussed above and may have radio-opaque markers along its length.

Figure 6:
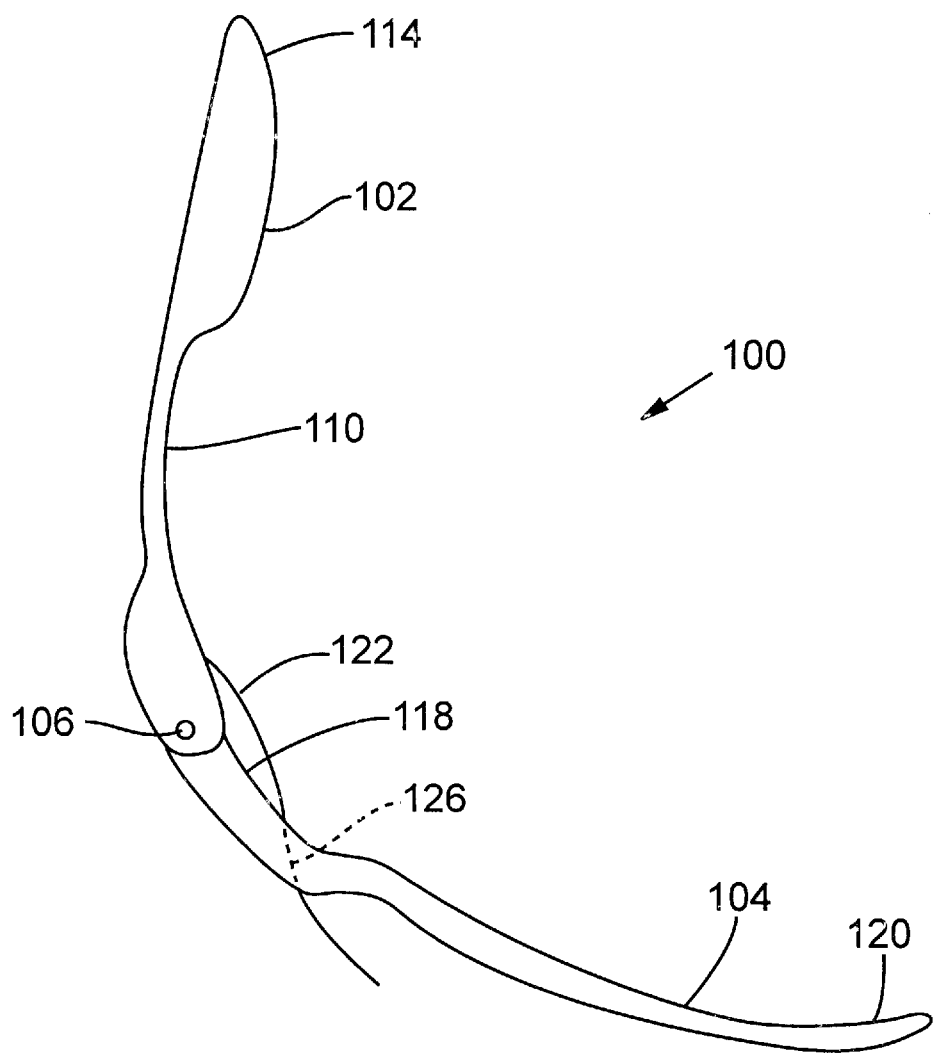
FIG. 6 is a side elevation view of a second embodiment of the prosthetic device of the present invention.

FIG. 6 is a side view of a prosthetic device 100 that includes a distal segment 102 connected to a proximal segment 104 via a pivot or hinged joint 106. In order to prevent the prosthetic device from sliding off of the valve annulus, hinged portion of the distal and proximal sections may be thicker than the remainder of the distal and proximal sections, this thickening buttressing prosthetic device 100 against the inner surface of coronary sinus 2 and functioning as an anchor, keeping prosthetic device 100 in its proper position.

Distal segment 102 has a narrow intermediate section 110 positioned between an interior section in the form of a clevis fastener 112 (shown in FIG. 7) and a free end section 114. Free end section 114 preferably has a bulbous shape, which contributes to the anchoring of the prosthetic device in coronary sinus 2 at a location that may eliminate or reduce compression of obtuse marginal arteries 116 (shown in FIG. 8) lying against an outer wall 117 of the valve annulus. Proximal segment 104 has an interior tongue section 118 that fits into clevis fastener 112 and a narrow free end section 120. Narrow free end section 120 need not be more narrow than free end section 114. The narrow free end section 120 may extend into the right atrium.

A control wire 122 is anchored on distal segment 102 and has a threaded section that passes through a mated threaded aperture 126 in interior tongue section 118 of proximal segment 104. Control wire 122 controls the angle between the distal and proximal sections and prohibits non-rotational motion. To that end, rotation of control wire 122 pivotally moves the distal and proximal segments closer to or farther from each other to, respectively, reduce or increase the circumference of the valve annulus.

Figures 7, 8:
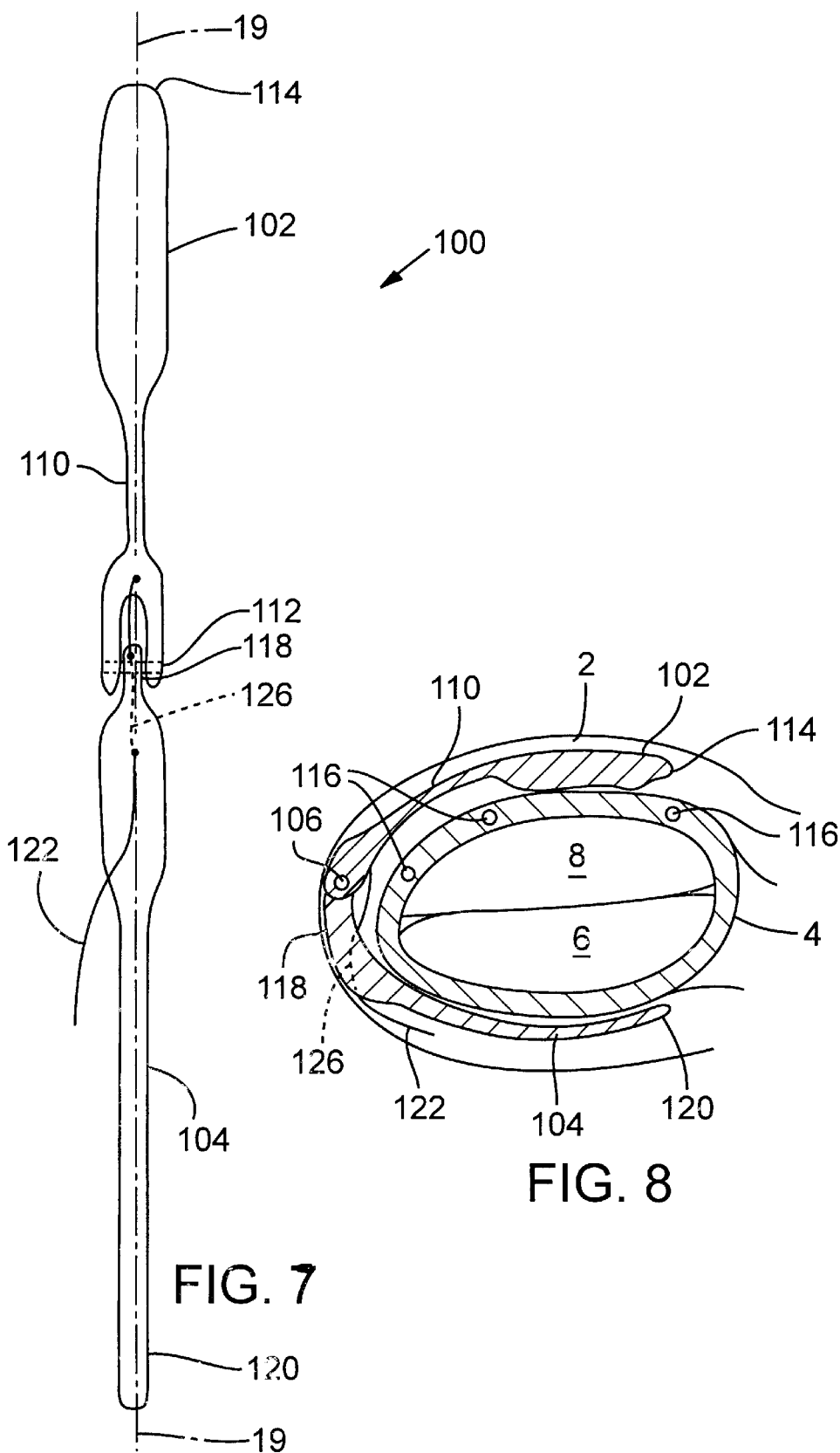
FIG. 7 is a plan elevation view of the prosthetic device of FIG. 6.
FIG. 8 is a schematic diagram of the prosthetic device of FIG. 6 deployed inside the coronary sinus.

FIG. 7 is a plan view of prosthetic device 100 that shows the interrelationship between the distal and proximal segments and their connection via clevis fastener 112.

FIG. 8 is a schematic diagram showing prosthetic device 100 positioned inside coronary sinus 2. Prosthetic device 100 may be inserted percutaneously into the coronary sinus using a single wire detachable and reattachable catheter. Once the prosthetic device is inside the coronary sinus, control wire 122 is rotated to pivotally move the distal and proximal segments closer together and thereby place a compression force on the mitral or tricuspid valve annulus, which compresses and reshapes the valve annulus. By reshaping the valve annulus, the anterior 6 and posterior 8 leaflets are pushed closer together, reducing the severity of valve regurgitation and restoring normal and efficient valve operation. Distal and proximal segments 102 and 104 preferably lie at about an 180 degree angle relative to one another.

Prosthetic devices 12 and 100 are preferably molded from a stiff, biocompatible material. One exemplary material is titanium. Alternatively, the components may be clothed in a biocompatible sheet or coated with a biocompatible material such as polytetrafluoroethylene, which sold under the trademark Teflon®.

There are many benefits of using the prosthetic device of the present invention instead of the prior art annuloplasty ring. Since the prosthetic device may be percutaneously implanted, there is no need for stopping the heart or opening the chest. Thus mitral valve repair may be performed on patients formerly unable to pursue such repair because they were thought to be too high risk for open-heart surgery. Unlike the insertion of an annuloplasty ring, no suturing is required for placement of the prosthetic device of the present invention, thereby eliminating any bulky knots that may be left in the bloodstream and which may result in thrombus or embolism. Because the prosthetic device of the present invention may be adjusted following insertion, corrections may be implemented. Finally, the prosthetic device of the present invention may be installed in a child since it can be removed and replaced with a larger prosthesis as necessary as the child grows.

It will be obvious to those having skill in the art that many changes may be made to the details of the above-described embodiments of this invention without departing from the underlying principles thereof. For example, although its use has been described with reference to a mitral valve, skilled persons will appreciate that the prosthetic device of the present invention may be deployed in a blood vessel surrounding the tricuspid valve such that severity of valve regurgitation in the tricuspid valve is decreased. The scope of the present invention should, therefore, be determined only by the following claims.

What is claimed is:

1. A method of decreasing the severity of valve regurgitation in a human heart having a gap between a posterior and an anterior leaflet through which blood flows backwards during ventricular contraction, the posterior and anterior leaflets connected to a valve annulus that includes an outer wall against which multiple marginal arteries lie to carry blood flow, the outer wall positioned adjacent to a blood vessel having an inner surface, the method comprising:

inserting into the blood vessel a prosthetic device having opposite terminal ends and a nonuniform thickness with a section of greater thickness, the prosthetic device comprised of multiple segments operatively connected to form a unitary structure, the segments aligned to define a curved longitudinal axis of the prosthetic device and interconnected to impart additional curvature of the longitudinal axis in response to an applied force;

positioning the prosthetic device in the blood vessel so that the section of greater thickness contacts the inner surface of the blood vessel in a region sufficiently remote from the marginal arteries such that blood flow through them is substantially unaffected in response to the application of a compression force against the outer wall of the valve annulus;

applying a force to the prosthetic device to impart the additional curvature of the longitudinal axis in a direction that brings the terminal ends toward each other and thereby applies to the outer wall of the valve annulus a compression force effective to urge the leaflets into close apposition and thereby decrease severity of valve regurgitation; and anchoring the prosthetic device to maintain the additional curvature of its longitudinal axis and thereby keep the prosthetic device in place to maintain the effective compression force.

2. The method of claim 1, further comprising:

rotating a control wire that is connected to one of the multiple segments to accomplish the bringing of the opposite terminal ends toward each other and thereby cause the application of a compression force to the outer wall of the valve annulus.

3. The method of claim 1, in which the human heart has a mitral valve annulus and a tricuspid valve annulus, and in which the valve annulus to which the compression force is applied is the mitral valve annulus.

4. The method of claim 1, in which the human heart has a mitral valve annulus and a tricuspid valve annulus, and in which the valve annulus to which the compression force is applied is the tricuspid valve annulus.

5. The method of claim 1, in which the prosthetic device is molded from titanium.

6. The method of claim 1, in which the prosthetic device is coated with polytetrafluoroethylene material.

7. The method of claim 1, in which the multiple segments include a distal segment pivotally connected to a proximal segment, the distal segment having a distal intermediate section positioned between a distal terminal end and a distal interior section, and the proximal segment having a proximal intermediate section positioned between a proximal terminal end and the proximal interior section, the distal interior section being pivotally connected to the proximal interior section.

8. The method of claim 7, in which the distal terminal end constitutes the section of greater thickness and is thicker than the distal interior section and distal intermediate section to buttress the prosthetic device against the outer wall of the valve annulus and thereby anchor the prosthetic device in its proper position.

9. The method of claim 7, in which a control wire anchored on the distal interior section includes a threaded portion that passes through a mated opening located in the proximal interior section, and in which rotation of the control wire pivotally moves the distal and proximal segments closer to each other to apply the compression force against the outer wall of the valve annulus.

* * * * *